United States Patent
Hsieh et al.

(10) Patent No.: US 7,456,289 B2
(45) Date of Patent: Nov. 25, 2008

(54) ANTI-TUMOR COMPOUNDS

(75) Inventors: Hsing-Pang Hsieh, Taipei (TW);
Yu-Sheng Chao, Warren, NJ (US);
Jing-Ping Liou, Taipei (TW);
Jang-Yang Chang, Taipei (TW);
Yen-Shih Tung, Taipei (TW)

(73) Assignee: National Health Research Institutes, Miaoli County (TW)

( * ) Notice: Subject to any disclaimer, the term of this patent is extended or adjusted under 35 U.S.C. 154(b) by 0 days.

(21) Appl. No.: 11/300,873

(22) Filed: Dec. 15, 2005

(65) Prior Publication Data

US 2006/0148801 A1 Jul. 6, 2006

Related U.S. Application Data

(60) Provisional application No. 60/641,218, filed on Dec. 31, 2004.

(51) Int. Cl.
C07D 401/00 (2006.01)
(52) U.S. Cl. ............... 546/277.4; 546/276.4; 546/276.7
(58) Field of Classification Search .............. 546/276.4, 546/276.7, 277.4
See application file for complete search history.

(56) References Cited

U.S. PATENT DOCUMENTS

| | | |
|---|---|---|
| 3,557,142 A | 1/1971 | Bell |
| 5,013,837 A | 5/1991 | Ward et al. |
| 5,468,898 A | 11/1995 | Huang et al. |
| 5,486,525 A | 1/1996 | Summers et al. |
| 5,753,664 A | 5/1998 | Aono et al. |
| 5,760,040 A | 6/1998 | Yoshida et al. |
| 6,013,648 A | 1/2000 | Rinaldi et al. |
| 6,162,930 A | 12/2000 | Pinney et al. |
| 6,350,777 B2 | 2/2002 | Pinney et al. |
| 6,515,141 B1 | 2/2003 | Goto et al. |
| 6,787,651 B2 | 9/2004 | Stolle et al. |
| 6,933,316 B2 | 8/2005 | Hsieh et al. |
| 2004/0167030 A1 | 8/2004 | Bernotas et al. |
| 2004/0259936 A1 | 12/2004 | Nagarkatti et al. |
| 2006/0030583 A1 | 2/2006 | Arnold et al. |
| 2007/0049615 A1 | 3/2007 | Ibrahim et al. |

FOREIGN PATENT DOCUMENTS

| | | |
|---|---|---|
| DE | 199 47 863 A1 | 4/2001 |
| WO | WO 92/06088 | 4/1992 |
| WO | WO93/13099 | 7/1993 |
| WO | WO 95/14003 | 5/1995 |
| WO | WO 98/08818 | 3/1998 |
| WO | WO 00/48606 A1 | 8/2000 |
| WO | WO 00/51983 | 9/2000 |
| WO | WO00/53582 | 9/2000 |
| WO | WO 01/09103 A2 | 2/2001 |
| WO | WO 01/19794 A2 | 3/2001 |
| WO | WO 01/19794 A3 | 3/2001 |
| WO | WO 01/28557 A1 | 4/2001 |
| WO | WO 01/68654 A2 | 9/2001 |
| WO | WO02/36561 | 5/2002 |
| WO | WO 02/36561 A1 | 5/2002 |
| WO | WO02/36597 | 5/2002 |
| WO | WO 02/50007 A2 | 6/2002 |
| WO | WO 02/060872 A1 | 8/2002 |
| WO | WO03/101990 | 12/2003 |
| WO | WO2004/009600 | 1/2004 |
| WO | WO2006/015123 | 2/2006 |

OTHER PUBLICATIONS

Angiogenesis [internet May 1, 2007] http://cancer.gov/cancertopics/understandingcancer/angiogenesis/Slide26>.
Angiognesis Inhibitors in the Treatment of Cancer, [internet May 1, 2007] <http://www.cancer.gov/cancertopis/factsheet/Therapy/angiogenesis-inhibitors/print?page=&keyword=)>.
Goloub et al., Oct. 15, 1999, Science, 286: 531-537.
Goto et al., 2000, STN International CAPLUS database, Columbus, Ohio, Accession No. 2001:167965.
Griffioen et al., Pharmacological Reviews 52(2):237-268 2000.
Homma et al., Journal of National Cancer Institute, 89(11):803-807 Jun. 1997.
Hortobagyi, G., Oct. 1, 1998, N. Eng. J. Med., 339:974-984.
Kimmel et al., J. Neurosurg. 66:161-171 1987.
Kuo et al., "BPR0L075, A Novel Synthetic Indole Compound with Antimitotic Activity in Human Cancer Cells, Exerts Effective Antitumoral Activity *in Vivo*," Cancer Research, 64:4621-4628 (2004).

(Continued)

*Primary Examiner*—James O. Wilson
*Assistant Examiner*—Paul V. Ward
(74) *Attorney, Agent, or Firm*—Occhiuti Rohlicek & Tsao LLP

(57) ABSTRACT

Compounds of the following formula:

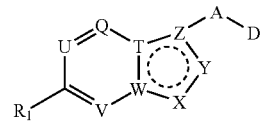

wherein A, D, Q, T, U, V, W, X, Y, Z, $R_1$, and ═ are as defined herein. This invention also relates to a method of inhibiting tubulin polymerization, or treating cancer or an angiogenesis-related disorder with one of these compounds.

29 Claims, No Drawings

OTHER PUBLICATIONS

Liou et al., "Concise Synthesis and Structure- Activity Relationships of Combretastatin A-4 Ananlgues, 1-Aroylindoles and 3-Aroylindoles, as Novel Classes of Potent Antitubulin Agents," J. Med. Chem. 47:4247-4257 (2004).

Minakata et al., "Functionalization of 1H-Pyrrolo[2,3-b]Pyridine," *The Chemical Society of Japan*, vol. 65 No. 11, pp. 2992-2997, (1992).

Powell et al., "Further Examples of Preferred Transition State Geometries in the Oxidative Cyclisation of Indole and Isoquinoline Derivatives," Tetrahedron Letters, vol. 22, pp. 4751-4754, 1981.

Samson et al., Chemotherapy Sensitivity and Resistance Assays; A Systematic Review, Sep. 1, 2004, J. Clinical Oncology 22(11): 3618-3630.

Song et al., "Isomerism of Bis(7-azaindolyl)Methane," *Organic Letters*, vol. 4, No. 23, pp. 4049-4052, (2002).

Yakhontov et al., "Derivatives of 7-Azaindole XV Electrophilic Substitution in 4-Methyl-7-Azaindole and Its Derivatives," (UDC 547.836.3) S. Ordzhonikidze All-Union Scientific Research Institute for Chemical Pharmaceutics, 1(11):2032-2040 (1965) (Original Article Submitted Jul. 20, 1964).

Yakhontov et al., "Derivatives of 7-Azaindole. XV. Electrophilic substation of 4-methyl-7-azaindole and its Derivatives." *Zhurnal Obshchei Khimii*, vol. 1 No. 11, pp. 2032-2040, (1965).

Yeung et al., "Friedel-Crafts Acylation of Indoles in Acidic Imidazolium Chloroaluminate Ionic Liquid at Room Temperature," *Tetrahedron Letters*, Vol. No. 43, pp. 5793-5795, (2002).

ANTI-TUMOR COMPOUNDS

CROSS REFERENCE TO RELATED APPLICATIONS

Pursuant to 35 USC § 119(e), this application claims priority to U.S. Provisional Application Ser. No. 60/641,218, filed Dec. 31, 2004, the contents of which are incorporated herein by reference.

BACKGROUND

Cancer treatment can be approached by several modes of therapy, including surgery, radiation, chemotherapy, or a combination of any of these treatments. Among them, chemotherapy is indispensable for inoperable or metastatic forms of cancer.

The microtubule system of eukaryotic cells is an important target for developing anti-cancer agents. More specifically, tubulin polymerization/depolymerization is a popular target for new chemotherapeutic agents. A variety of clinically used compounds (e.g., paclitaxel, epothilone A, vinblastine, combretastatin A-4, dolastatin 10, and colchicine) target tubulin polymerization/depolymerization and disrupt cellular microtubule structures, resulting in mitotic arrest and inhibition of the growth of new vascular epithelial cells. See, e.g., Jordan et al. (1998) *Med. Res. Rev.* 18: 259-296. Thus, those compounds may have the ability to inhibit excessive angiogenesis, which occurs in diseases such as cancer (both solid and hematologic tumors), cardiovascular diseases (e.g., atherosclerosis), chronic inflammation (e.g., rheutatoid arthritis or Crohn's disease), diabetes (e.g., diabetic retinopathy), macular degeneration, psoriasis, endometriosis, and ocular disorders (e.g., corneal or retinal neovascularization). See, e.g., Griggs et al. (2002) *Am. J. Pathol.* 160(3): 1097-103.

Take combretastatin A-4 (CA-4) for example. CA-4, isolated by Pettit and co-workers in 1982 (*Can. J. Chem.* 60: 1374-1376), is one of the most potent anti-mitotic agents derived from the stem wood of the South African tree *Combretum caffrum*. This agent shows strong cytotoxicity against a wide variety of human cancer cells, including multi-drug resistant cancer cells. See, e.g., Pettit et al. (1995) *J. Med. Chem.* 38: 1666-1672; Lin et al. (1989) *Biochemistry* 28: 6984-6991; and Lin et al. (1988) *Mol. Pharmacol.* 34: 200-208. CA-4, structurally similar to colchicines, possesses a higher affinity for the colchicine binding site on tubulin than colchicine itself. Pettit et al. (1989) *Experientia* 45: 209-211. It also has been shown to possess anti-angiogenesis activity. See Pinney et al. WO 01/68654A2. The low water-solubility of CA-4 limits its efficacy in vivo. See, e.g., Chaplin et al. (1999) *Anticancer Research* 19: 189-195; and Grosios et al. (1999) *Br. J. Cancer* 81: 1318-1327.

Identification of compounds that also target the microtubule system (e.g., tubulin polymerization/depolymerization) can lead to new therapeutics useful in treating or preventing cancer or symptoms associated with cancer.

SUMMARY

This invention is based on a surprising discovery that a group of fused bicyclic heteroaryl compounds effectively inhibit the growth of certain cancer cells.

In one aspect, this invention features fused bicyclic heteroaryl compounds.

One subset of the fused bicyclic heteroaryl compounds have the following formula:

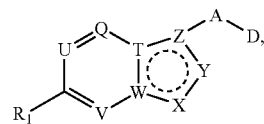

in which each $=$ is a single bond or a double bond; A is C(=O), CRR', O, NR, S, SO, or $SO_2$; D is aryl or hetereoaryl; $R_1$ is selected from H, alkyl, aryl, alkoxy, hydroxy, halo, amino, or alkylamino; each of Q, U, V, and Y, independently, is CR or N; X is N, CR, or NR'; Z is C; and each of T and W is C or N, at least one of T and W being C; provided that when T is C and W is N, the bond between T and W is a single bond, the bond between T and Z is a double bond, the bond between Y and Z is a single band, the bond between X and Y is a double bond, the bond between W and X is a single bond, and X is N or CR; when T is N and W is C, the bond between T and W is a single bond, the bond between T and Z is a single bond, the bond between Y and Z is a double band, the bond between X and Y is a single bond, the bond between W and X is a double bond, and X is N or CR; and when T is C and W is C, the bond between T and W is a double bond, the bond between T and Z is a single bond, the bond between Y and Z is a double band, the bond between X and Y is a single bond, the bond between W and X is a single bond and X is NR and Y is N, or X is NR, Y is CR, and at least one of Q, U and V is N. Each of R and R', independently, is H, alkyl, alkenyl, alkynyl, aryl, heteroaryl, cyclyl, heterocyclyl, $SO_3R_a$, $SO_2R_a$, $SO_2NR_aR_b$, $COR_a$, $COOR_a$, or $CONR_aR_b$; each $R_a$ and $R_b$, independently, is H, alkyl, alkenyl, alkynyl, aryl, heteroaryl, cyclyl, or heterocyclyl.

Referring to this formula, the compounds may have the following feature: each of T and X is N, W is C, each of Q, U, and V is CH, and Y is CR; each of T and W is C, X is NH, Y is N, and each of Q, U, and V is CH; each of T and W is C, each of Q and U is CH, V is N, X is NH, and Y is CR; T is C, W is N, each of Q, U, V, and X is CH, and Y is CR; T is N, W is C, each of Q, U, V, and X is CH, and Y is CR; T is C, W is N, each of Q, U, and V, is CH, X is N, and Y is CR; each of T and W is C, each of Q, U, and V is CH, X is O, and Y is N; each of T and W is C, Q is CH, or each of U and V is N, X is NH, and Y is CR; or T is C, each of W, V, and X is N, each of Q and U is CH, and Y is CR. Further, the compounds may have one or more of the following features: D is substituted phenyl, e.g., 3,4,5-trimethoxyphenyl; A is C(O); and A is $CH_2$, NH, O, S, or $SO_2$.

Another subset of the fused bicyclic heteroaryl compounds have the following formula:

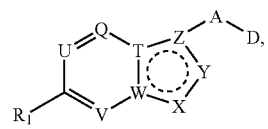

in which each $=$ is a single bond or a double bond; A is C(=O), CRR', O, NR, S, SO, or $SO_2$; D is aryl or hetereoaryl; $R_1$ is selected from alkyl, aryl, alkoxy, hydroxy, halo, amino, or alkylamino; each of Q, U, or V, independently, is CR or N; X is O or S; Y is CR" or N; each of T, W, and Z is C; the bond between T and W is a double bond; the bond between T and Z is a single bond; the bond between Y and Z is a double band; the bond between X and Y is a single bond; and the bond between W and X is a single bond. Each of R and R', independently, is H, alkyl, alkenyl, alkynyl, aryl, heteroaryl, cyclyl, heterocyclyl, $SO_3R_a$, $SO_2R_a$, $SO_2NR_aR_b$, $COR_a$, $COOR_a$, or $CONR_aR_b$, and R" is H, alkyl, alkenyl, alkynyl, heteroaryl, cyclyl, heterocyclyl, $SO_3R_a$, $SO_2R_a$, $SO_2NR_aR_b$, $COR_a$, $COOR_a$, or $CONR_aR_b$; each $R_a$ and $R_b$, independently, is H, alkyl, alkenyl, alkynyl, aryl, heteroaryl, cyclyl, or heterocyclyl.

Referring to the above formula, the compounds may have one or more of the features: each of Q, U, and V is CH, and Y is CR; D is substituted phenyl, e.g., 3,4,5-trimethoxyphenyl; A is C(O); and Y is CH, $CNH_2$, $CCH_3$, or $CCH_2CH_3$.

The term "alkyl" herein refers to a straight or branched hydrocarbon, containing 1-10 carbon atoms. Examples of alkyl groups include, but are not limited to, methyl, ethyl, n-propyl, i-propyl, n-butyl, i-butyl, and t-butyl. The term "alkenyl" refers to a straight or branched hydrocarbon, containing 1-10 carbon atoms and one or more double bonds. The term "alkynyl" refers to a straight or branched hydrocarbon, containing 1-10 carbon atoms and one or more triple bonds. The term "alkoxy" refers to an —O-alkyl. The term "amino" refers to a nitrogen radical which is bonded to two hydrogen, or one hydrogen and one alkyl groups, or two alkyl groups.

The term "aryl" refers to a 6-carbon monocyclic, 10-carbon bicyclic, 14-carbon tricyclic aromatic ring system wherein each ring may have 1 to 4 substituents. Examples of aryl groups include, but are not limited to, phenyl, naphthyl, and anthracenyl. The term "aryloxy" refers to an —O-aryl. The term "aralkyl" refers to an alkyl group substituted with an aryl group.

The term "cyclyl" refers to a saturated and partially unsaturated cyclic hydrocarbon group having 3 to 12 carbons. Examples of cyclyl groups include, but are not limited to, cyclopropyl, cyclobutyl, cyclopentyl, cyclopentenyl, cyclohexyl, cyclohexenyl, cycloheptyl, and cyclooctyl.

The term "heteroaryl" refers to an aromatic 5-8 membered monocyclic, 8-12 membered bicyclic, or 11-14 membered tricyclic ring system having one or more heteroatoms (such as O, N, or S). Examples of heteroaryl groups include pyridyl, furyl, imidazolyl, benzimidazolyl, pyrimidinyl, thienyl, quinolinyl, indolyl, and thiazolyl. The term "heteroaralkyl" refers to an alkyl group substituted with a heteroaryl group.

The term "heterocyclyl" refers to a nonaromatic 5-8 membered monocyclic, 8-12 membered bicyclic, or 11-14 membered tricyclic ring system having one or more heteroatoms (such as O, N, or S). Examples of heterocyclyl groups include, but are not limited to, piperazinyl, pyrrolidinyl, dioxanyl, morpholinyl, and tetrahydrofuranyl.

Alkyl, alkenyl, alkynyl, cyclyl, heterocyclyl, aryl, heteroaryl, and alkoxy mentioned herein include both substituted and unsubstituted moieties. Examples of substituents include, but are not limited to, halo, hydroxyl, amino, cyano, nitro, mercapto, alkoxycarbonyl, amido, carboxy, alkanesulfonyl, alkylcarbonyl, carbamido, carbamyl, carboxyl, thioureido, thiocyanato, sulfonamido, alkyl, alkenyl, alkynyl, alkyloxy, aryl, heteroaryl, cyclyl, heterocyclyl, in which alkyl, alkenyl, alkynyl, alkyloxy, aryl, heteroaryl cyclyl, and heterocyclyl are optionally further substituted.

Shown below are some examples of the bicyclic heteroaryl compounds of this invention:

Compound 1
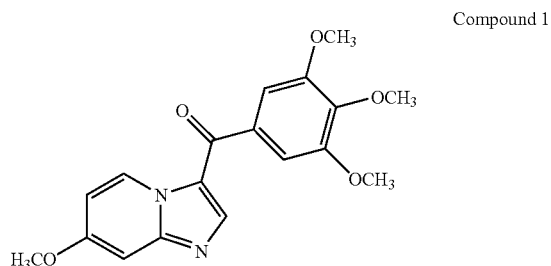

Compound 2
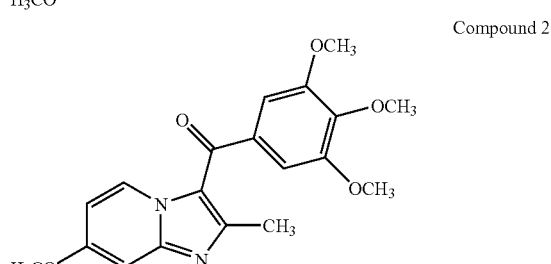

Compound 3
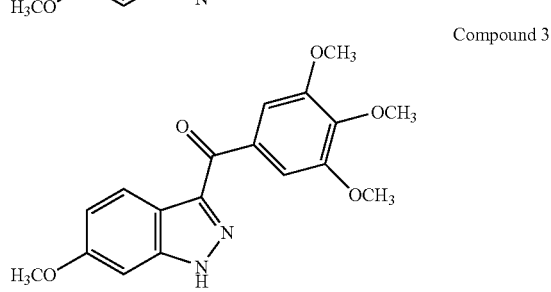

Compound 4
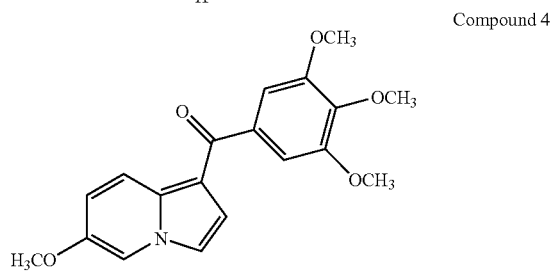

Compound 5
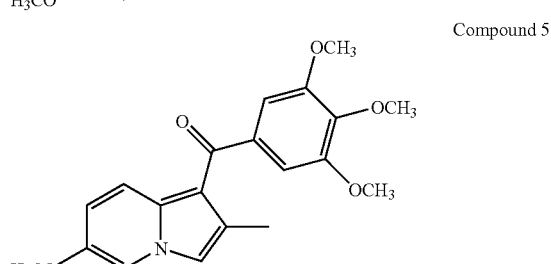

Compound 6
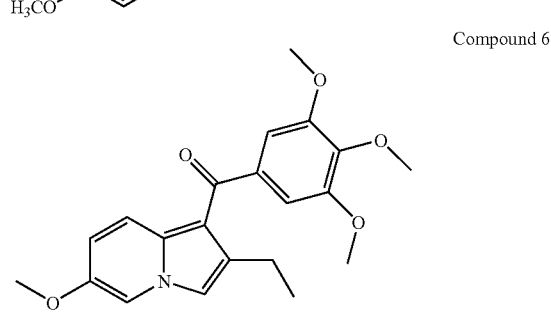

Compound 7
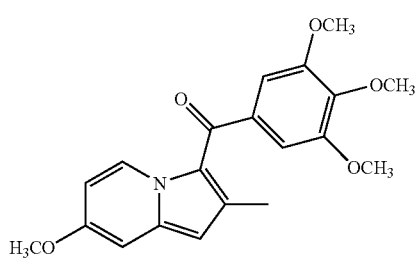
Compound 8
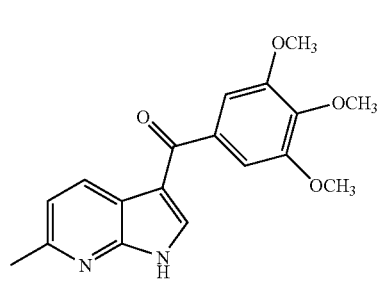
Compound 9
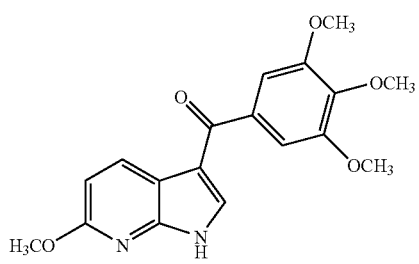
Compound 10
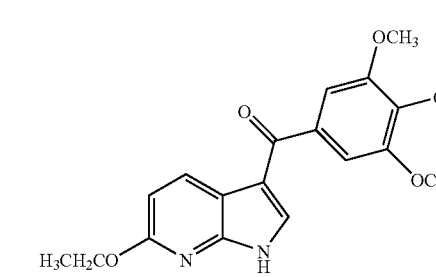
Compound 11
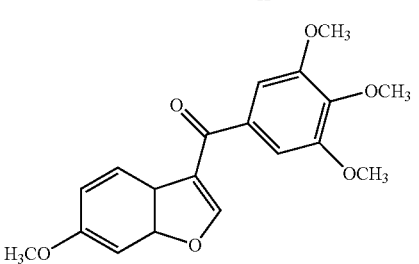
Compound 12
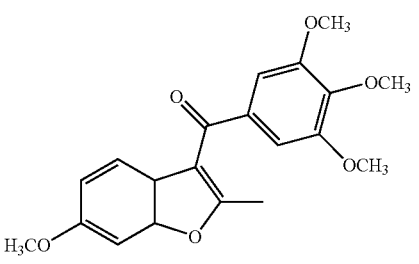
Compound 13
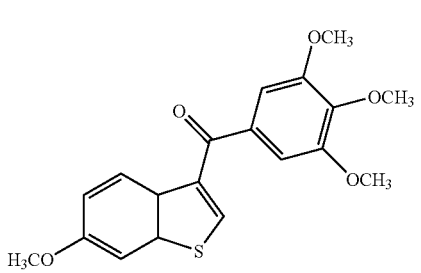
Compound 14
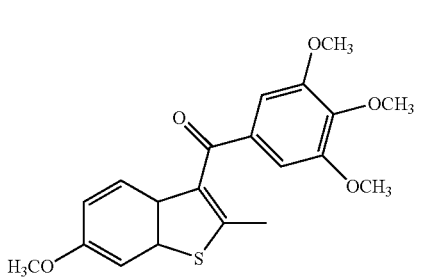
Compound 15
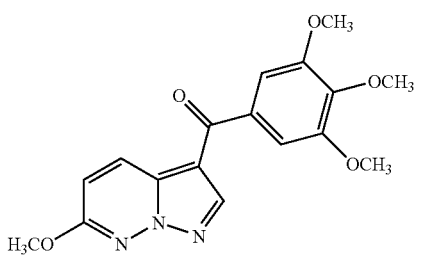
Compound 16
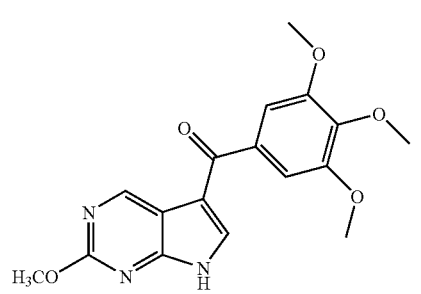
Some other examples of the compounds of this invention are shown below:
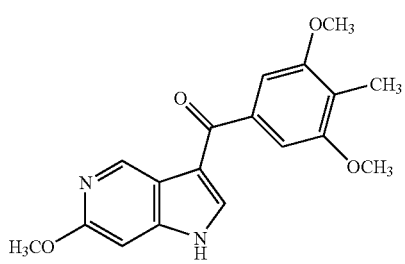

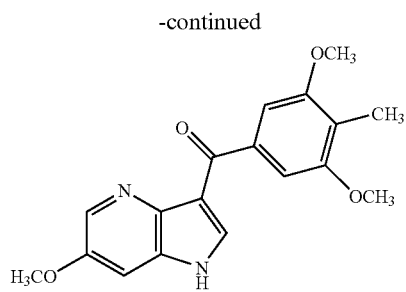
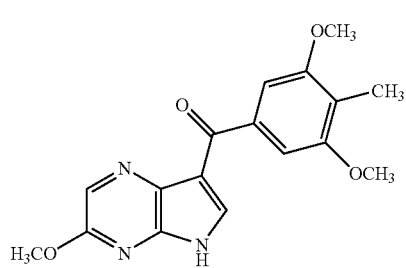
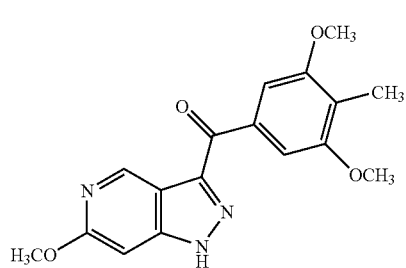
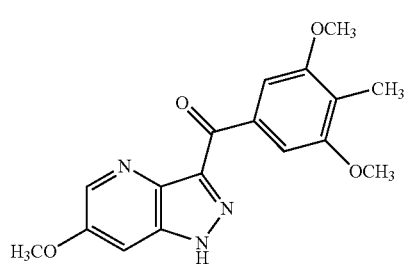
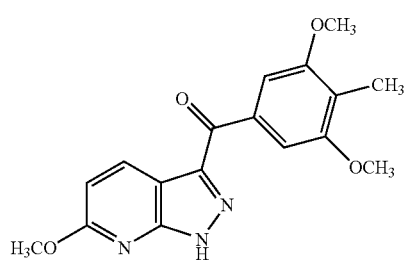
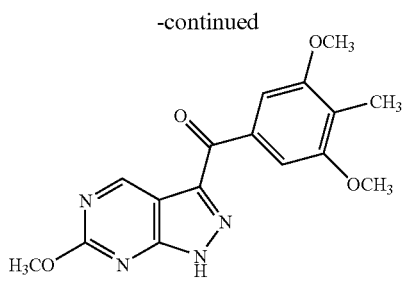
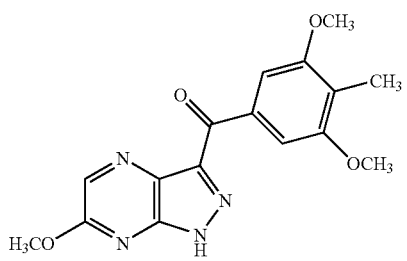
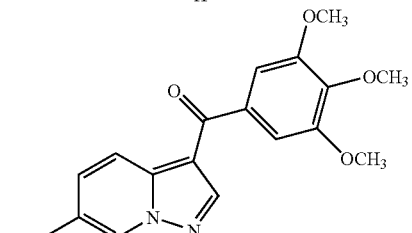
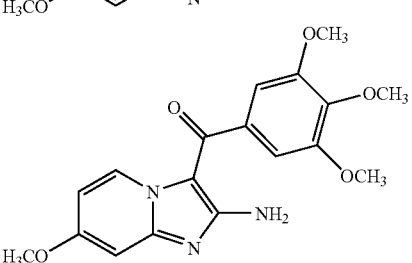
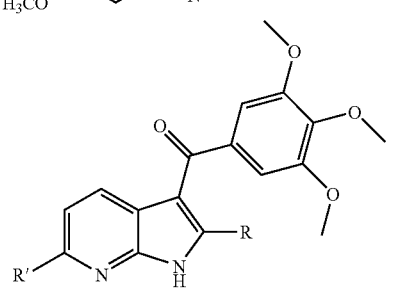
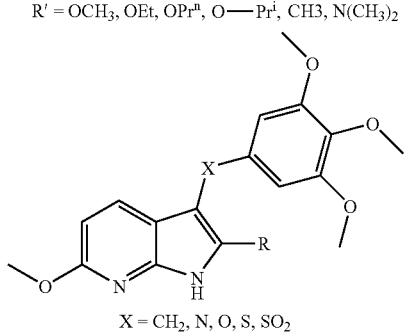
R = H, CH₃
R' = OCH₃, OEt, OPr$^n$, O—Pr$^i$, CH3, N(CH₃)₂
X = CH₂, N, O, S, SO₂

-continued

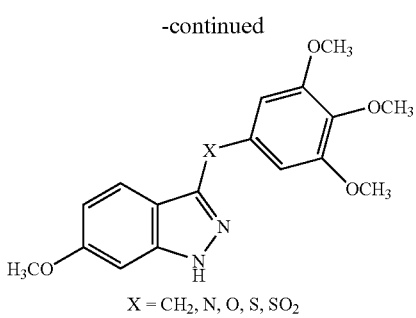

X = CH₂, N, O, S, SO₂

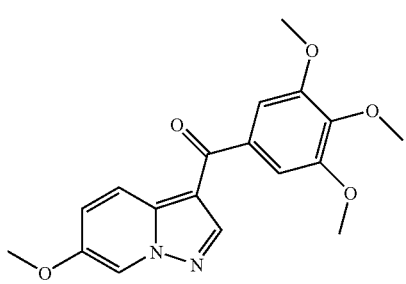

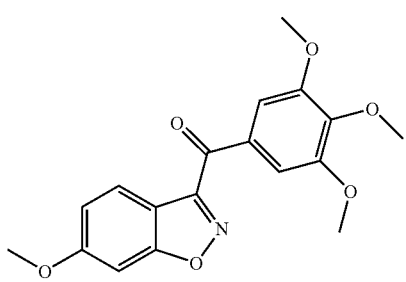

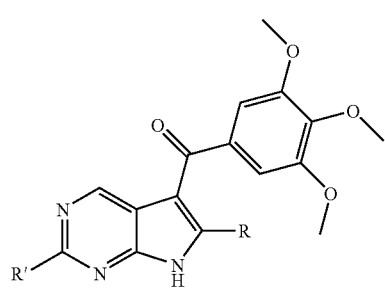

R = H, CH₃
R' = OCH₃, OEt, OPr$^n$, O—Pr$^i$, CH3, N(CH₃)₂

The bicyclic heteroaryl compounds described above inhibit cancer cell growth. Thus, in another aspect, this invention also features a method for treating cancer. The method includes administering to a subject in need thereof an effective amount of one of the above-mentioned compounds.

In still another aspect, this invention features a method for inhibiting tubulin polymerization, or treating an angiogenesis-related disorder. The method includes administering to a subject in need thereof an effective amount of one or more of the above-mentioned compounds.

Also within the scope of this invention is a composition containing one or more of the above-described compounds for use in treating cancer or an angiogenesis-related disorder, as well as the use of such a composition for the manufacture of a medicament for treating cancer or an angiogenesis-related disorder.

The details of many embodiments of the invention are set forth in the description below. Other features, objects, and advantages of the invention will be apparent from the description and the claims.

DETAILED DESCRIPTION

The fused dicyclic heteroaryl compounds described above can be prepared by methods well known in the art. For example, synthesis of indazole, imidazo[1,2-a]pyridine, 1H-pyrrolo[2,3-b]pyridine, indolizine, pyrazolo[1,5-a]pyridine, benzo[d]isoxazole, and 7H-pyrrolo[2,3-d]pyrimidine has been described in the literature. See, e.g., Chemistry of Heterocyclic Compounds, Vol. 22, Edited by Richard H. Wiley, Published by Interscience Publishers, New York, 1967. One skilled in the art can modify these methods and make the fused dicyclic heteroaryl compounds of this invention. Shown in Schemes 1-4 are synthetic routes for compounds 1, 2, 3, and 7, respectively.

Scheme 1:

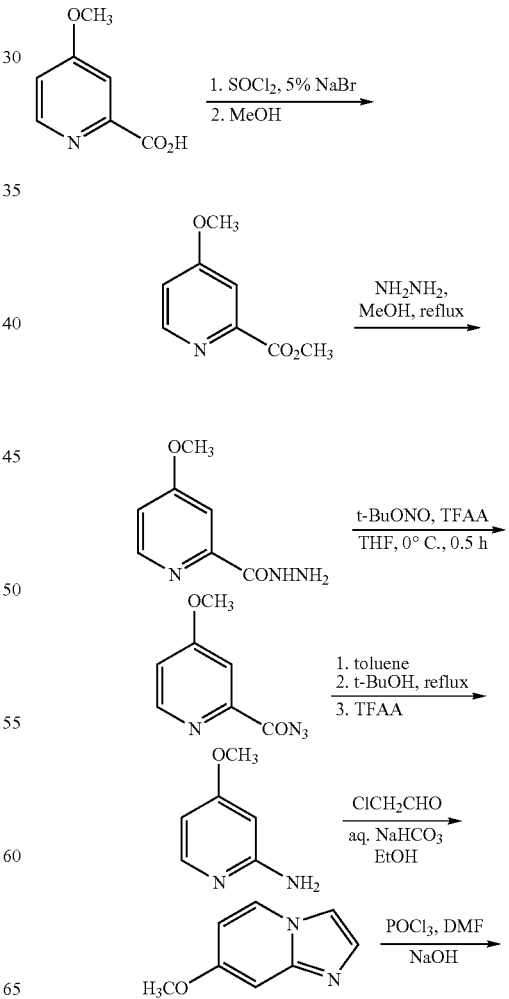

-continued
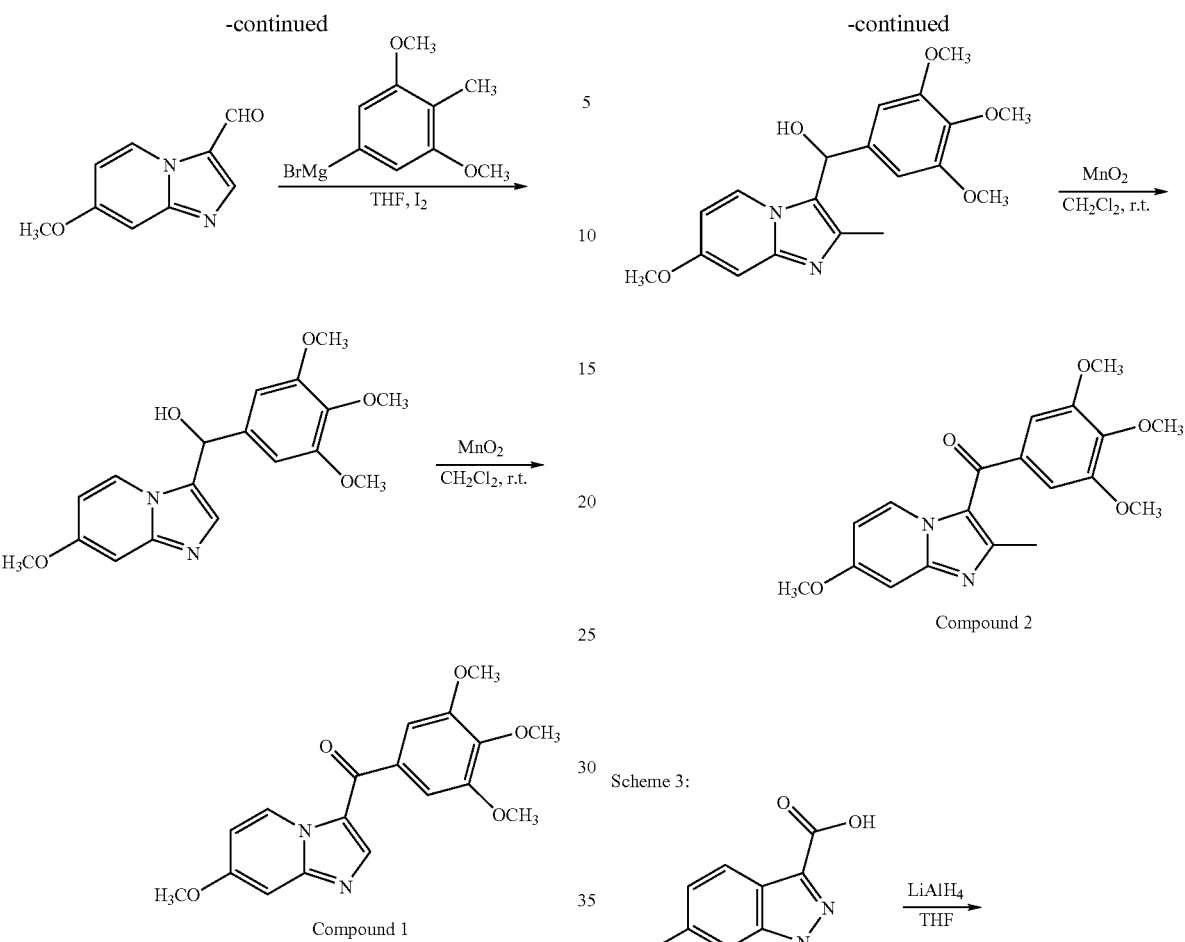
Scheme 2:
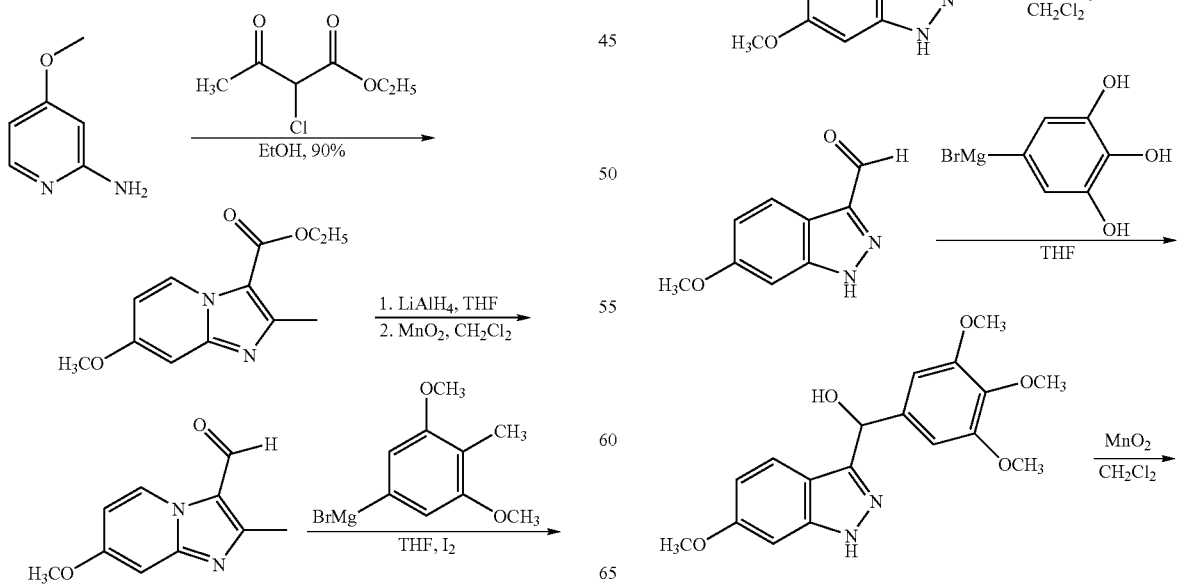

-continued

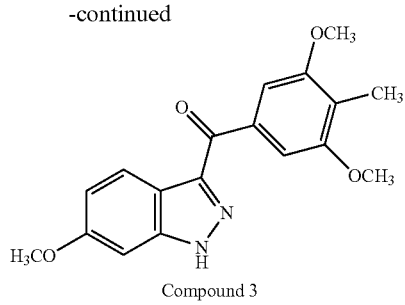

Compound 3

A synthesized fused bicyclic heterocyclic compound can be further purified by flash column chromatography, high performance liquid chromatography, or crystallization.

Also within the scope of this invention is a pharmaceutical composition that contains an effective amount of at least one fused bicyclic heterocyclic compound of this invention and a pharmaceutically acceptable carrier. Further, this invention covers a method for inhibiting tubulin polymerization or treating cancer or an angiogenesis-related disorder. The method includes administering to a subject an effective amount of a fused bicyclic heterocyclic compounds described in the "Summary" section.

As used herein, the term "treating" refers to administering a fused bicyclic heteroaryl compound to a subject that has a Scheme 4:

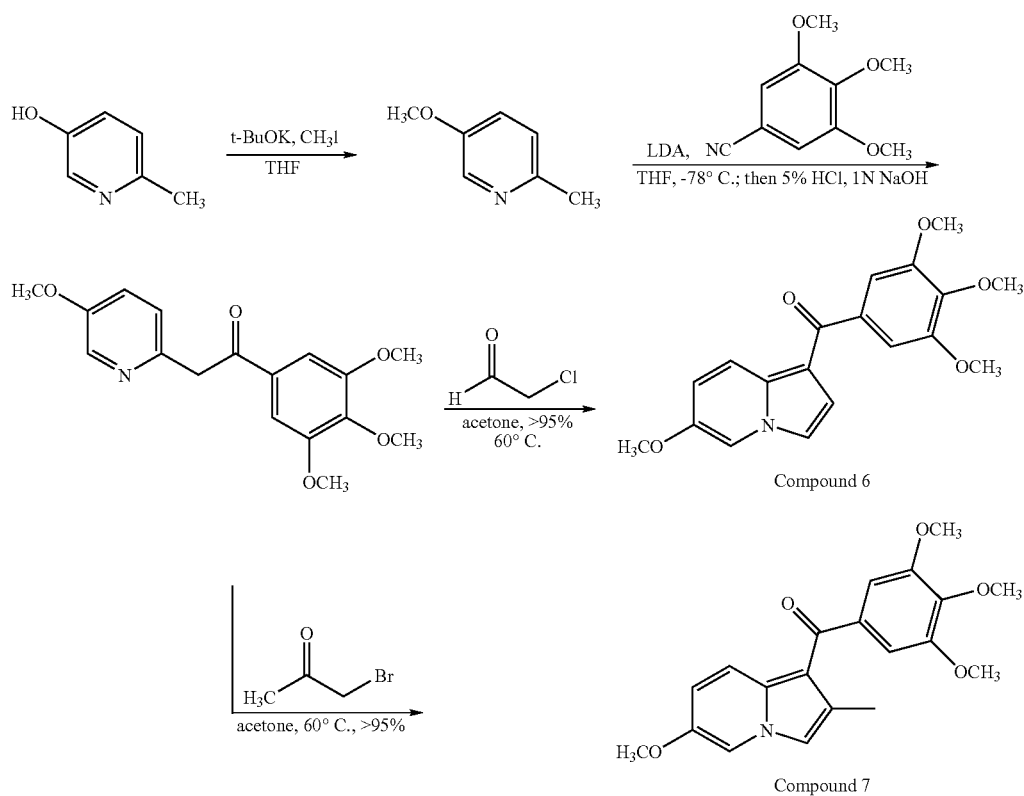

To synthesize the compounds of this invention, suitable synthetic chemistry transformations and protecting group methodologies (protection and deprotection) may be used. These transformations and methodologies are known in the art and include, for example, those described in R. Larock, *Comprehensive Organic Transformations*, VCH Publishers (1989); T. W. Greene and P. G. M. Wuts, *Protective Groups in Organic Synthesis*, 3rd Ed., John Wiley and Sons (1999); L. Fieser and M. Fieser, *Fieser and Fieser's Reagents for Organic Synthesis*, John Wiley and Sons (1994); and L. Paquette, ed., *Encyclopedia of Reagents for Organic Synthesis*, John Wiley and Sons (1995) and subsequent editions thereof.

disorder, e.g., cancer or an angiogenesis-related disorder, or has a symptom of such a disorder, or has a predisposition toward such a disorder, with the purpose to cure, heal, alleviate, relieve, alter, remedy, ameliorate, improve, or affect the disorder, the symptoms of the disorder, or the predisposition toward the disorder. The term "an effective amount" refers to the amount of the active agent that is required to confer the intended therapeutic effect in the subject. Effective amounts may vary, as recognized by those skilled in the art, depending on route of administration, excipient usage, and the possibility of co-usage with other agents.

As used herein, the term "cancer" refers to cells having the capacity for autonomous growth, i.e., an abnormal state or condition characterized by rapidly proliferating cell growth. In addition, cancer can be a drug resistance phenotype wherein cancer cells express P-glycoprotein, multidrug resistance-associated proteins, lung cancer resistance-associated proteins, breast cancer resistance proteins, or other proteins associated with resistance to anti-cancer drugs. Examples of cancers include, but are not limited to, carcinoma and sarcoma such as leukemia, sarcomas, osteosarcoma, lymphomas, melanoma, ovarian cancer, skin cancer, testicular cancer, gastric cancer, pancreatic cancer, renal cancer, breast cancer, prostate cancer, colorectal cancer, cancer of head and neck, brain cancer, esophageal cancer, bladder cancer, adrenal cortical cancer, lung cancer, bronchus cancer, endometrial cancer, nasopharyngeal cancer, cervical or hepatic cancer, or cancer of unknown primary site.

The term "angiogenesis" refers to the growth of new blood vessels—an important natural process occurring in the body. In many serious diseases states, the body loses control over angiogenesis. Angiogenesis-dependent diseases result when new blood vessels grow excessively. Examples of angiogenesis-related disorders include cardiovascular diseases (e.g., atherosclerosis), chronic inflammation (e.g., rheutatoid arthritis or Crohn's disease), diabetes (e.g., diabetic retinopathy), macular degeneration, psoriasis, endometriosis, and ocular disorders (e.g., corneal or retinal neovascularization).

To practice the method of the present invention, the above-described pharmaceutical composition can be administered orally, parenterally, by inhalation spray, topically, rectally, nasally, buccally, vaginally or via an implanted reservoir. The term "parenteral" as used herein includes subcutaneous, intracutaneous, intravenous, intramuscular, intraarticular, intraarterial, intrasynovial, intrasternal, intrathecal, intralesional and intracranial injection or infusion techniques.

A sterile injectable composition, e.g., a sterile injectable aqueous or oleaginous suspension, can be formulated according to techniques known in the art using suitable dispersing or wetting agents (such as Tween 80) and suspending agents. The sterile injectable preparation can also be a sterile injectable solution or suspension in a non-toxic parenterally acceptable diluent or solvent, for example, as a solution in 1,3-butanediol. Among the acceptable vehicles and solvents that can be employed are mannitol, water, Ringer's solution and isotonic sodium chloride solution. In addition, sterile, fixed oils are conventionally employed as a solvent or suspending medium (e.g., synthetic mono- or diglycerides). Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions can also contain a long-chain alcohol diluent or dispersant, or carboxymethyl cellulose or similar dispersing agents. Other commonly used surfactants such as Tweens or Spans or other similar emulsifying agents or bioavailability enhancers which are commonly used in the manufacture of pharmaceutically acceptable solid, liquid, or other dosage forms can also be used for the purposes of formulation.

A composition for oral administration can be any orally acceptable dosage form including, but not limited to, capsules, tablets, emulsions and aqueous suspensions, dispersions and solutions. In the case of tablets for oral use, carriers which are commonly used include lactose and corn starch. Lubricating agents, such as magnesium stearate, are also typically added. For oral administration in a capsule form, useful diluents include lactose and dried corn starch. When aqueous suspensions or emulsions are administered orally, the active ingredient can be suspended or dissolved in an oily phase combined with emulsifying or suspending agents. If desired, certain sweetening, flavoring, or coloring agents can be added. A nasal aerosol or inhalation composition can be prepared according to techniques well-known in the art of pharmaceutical formulation and can be prepared as solutions in saline, employing benzyl alcohol or other suitable preservatives, absorption promoters to enhance bioavailability, fluorocarbons, and/or other solubilizing or dispersing agents known in the art. A fused bicyclic heterocyclic compound-containing composition can also be administered in the form of suppositories for rectal administration.

The carrier in the pharmaceutical composition must be "acceptable" in the sense of being compatible with the active ingredient of the formulation (and preferably, capable of stabilizing it) and not deleterious to the subject to be treated. For example, solubilizing agents such as cyclodextrins, which form specific, more soluble complexes with the fused bicyclic heterocyclic compounds, or one or more solubilizing agents, can be utilized as pharmaceutical excipients for delivery of the fused bicyclic heterocyclic compounds. Examples of other carriers include colloidal silicon dioxide, magnesium stearate, cellulose, sodium lauryl sulfate, and D&C Yellow # 10.

Suitable in vitro assays can be used to preliminarily evaluate the efficacy of one or more of the fused bicyclic heterocyclic compounds in inhibiting growth of cancer cell lines. The compounds can further be examined for its efficacy in treating cancer by in vivo assays. For example, the compounds can be administered to an animal (e.g., a mouse model) having cancer and its therapeutic effects are then assessed. Based on the results, an appropriate dosage range and administration route can also be determined.

The fused bicyclic heterocyclic compounds described above can be screened for the efficacy in inhibiting tubulin polymerization and inhibiting angiogenesis by the methods described in the specific examples below.

Without further elaboration, it is believed that the above description has adequately enabled the present invention. The following specific embodiments are, therefore, to be construed as merely illustrative, and not limitative of the remainder of the disclosure in any way whatsoever. All of the publications cited herein are hereby incorporated by reference in their entirety.

EXAMPLES

Example 1

Synthesis of (7-methoxy-imidazo[1,2-a]pyridin-3-yl)-(3,4,5-trimethoxy-phenyl)-methanone (compound 1)

7-Methoxyimidazo[1,2-a]pyridine was prepared according to the method described in Loeber, S., et al., *Bioorg Med Chem Lett* 1999, 9 (1), 97-102.

7-Methoxyimidazo[1,2-a]pyridine (621 mg, 4.2 mmol) was mixed with $POCl_3$ (16.8 mmol) in dimethylformamide (4 mL). The reaction mixture was heated at 90° C. for 24 h and then cooled to room temperature. After the solvent was removed in vacuo, an oil was obtained. The oil was purified on a silica gel column eluting with EtOAc/Hexane (1:1) to afford 7-methoxyimidazo[1,2-a]pyridine-3-carbaldehyde (508 mg, 69%).

To a dry flask equipped with a condenser, an addition funnel, and a magnetic stirrer were added magnesium turnings (2.5 mmol), 0.5 mL of anhydrous tetrahydrofuran (THF), and a small piece of iodine. To this was added via the addition funnel approximately ⅓ of 3,4,5-trimethoxybromobenzene (2.5 mmol) in 1.3 mL of THF. When the solution became colorless (heating may be needed), the remaining 3,4,5-trimethoxybromobenzene solution was added dropwise to the solution under mild refluxing. The reaction mixture was stirred for 1 h at room temperature and then slowly added to 7-methoxyimidazo[1,2-a]pyridine-3-carbaldehyde (0.094 g, 0.53 mmol) in THF (3 mL) at 0° C. After the addition, the solution was allowed to stir at room temperature for another 20 min. Then, a saturated $NH_4Cl$ solution (5 mL) was slowly added at 0° C., and the mixture was stirred for 10 min. The aqueous layer was separated and extracted with $Et_2O$ (3×10 mL). The combined organic layers were washed with brine, dried over $MgSO_4$, and filtered. The filtrate was concentrated in vacuo and the residue was purified by column chromatography to provide benzhydrol (0.119 g).

$MnO_2$ (0.444 g, 5.1 mmol) was added to a solution of benzhydrol (0.115 g, 0.33 mmol) in 5 mL anhydrous $CH_2Cl_2$ at 0° C. with stirring. After the addition, the mixture was stirred at room temperature for 8 h. The mixture was diluted with anhydrous ether (50 mL) and filtered through a pad of Celite. The filtrate was concentrated in vacuo and the residue was purified by flash chromatography to give compound 1 (0.087 g, 76%).

$^1H$ NMR (300 MHz, $CDCl_3$) δ 3.92 (s, 9H, —$OCH_3$), 3.94 (s, 3H, —$OCH_3$), 6.83 (dd, 1H, J=7.5, 1.5 Hz), 7.11 (s, 2H), 7.12 (d, 1H, J=1.5 Hz), 8.16 (s, 1H), 9.49 (d, J=1H, 7.5 Hz)

Example 2

Synthesis of (7-methoxy-2-methyl-imidazo[1,2-a] pyridin-3-yl)-(3,4,5-trimethoxy-phenyl)-methanone (compound 2)

A mixture of 4-methoxy-2-aminopyridine (1.07 g, 8.6 mmol) and ethyl 2-chloroacetoacetate (5.4 g) in EtOH (50 mL) was refluxed for 24 h. The reaction mixture was then concentrated to half its volume, extracted with $CH_2Cl_2$, washed with brine and then water, and dried over anhydrous $MgSO_4$. The solvent was removed in vacuo and the residue was purified on a silica gel column eluting with EtOAc and then $MeOH/CH_2Cl_2$ (1:9) to give ethyl 7-methoxy-2-methylimidazo[1,2-a]pyridine-3-carboxylate (2.71 g, 90%).

A mixture of the resulting product (0.340 g, 1.04 mmol) in THF (15 mL) was stirred for 10 min at 0° C. under $N_2$. Lithium aluminum hydride (LAH) was added and the mixture stirred overnight at room temperature under $N_2$. An aqueous $NH_4Cl$ solution (5 mL) was then added. The mixture was concentrated to half its volume and extracted with EtOAc. The combined organic layers were washed with brine and water, dried over anhydrous $MgSO_4$, and evaporated to give a residue. $MnO_2$ (0.783 g, 9 mmol) was added to the residue in anhydrous $CH_2Cl_2$ (15 mL) at 0° C. with stirring. After the addition, the mixture was stirred at room temperature for 8 h, diluted with anhydrous ether (50 mL) and filtered through a pad of Celite. The filtrate was concentrated in vacuo and the residue was purified by flash chromatography to give 7-methoxy-2-methylimidazo[1,2-a]pyridine-3-carbaldehyde (0.070 g, 53%).

The resulting product was then reacted with 3,4,5-trimethoxybromobenzene and then oxidized by $MnO_2$ in a manner similar to that described in Example 1 to afford compound 2 at a yield of 55%.

$^1H$ NMR (300 MHz, $CDCl_3$) δ 2.22 (s, 3H, —$CH_3$), 3.89 (s, 6H, —$OCH_3$), 3.92 (s, 3H, —$OCH_3$), 3.93 (s, 3H, —$OCH_3$), 6.71 (dd, 1H, J=7.8, 2.4 Hz), 6.92 (s, 3H), 9.24 (d, 1H, J=7.8 Hz).

Example 3

Synthesis of (6-methoxy-3a,7a-dihydro-1H-indazol-3-yl)-(3,4,5-trimethoxy-phenyl)-methanone (compound 3)

A mixture of 6-methoxy-1H-indazole-3-carboxylic acid (0.200 g, 1.04 mmol) in THF (15 mL) was stirred for 10 min at 0° C. under $N_2$. LAH was added and the mixture was stirred overnight at room temperature under $N_2$. Then, an aqueous $NH_4Cl$ solution (5 mL) was added and the reaction mixture was concentrated to half its volume and extracted with EtOAc. The organic layer was washed with brine and water, dried over anhydrous $MgSO_4$, and the solvent removed in vacuo to give a residue. $MnO_2$ (0.680 g, 7.8 mmol) was added to the residue in anhydrous $CH_2Cl_2$ (15 mL) at 0° C. with stirring. After the addition, the mixture was stirred at room temperature for 8 h. The mixture was diluted with anhydrous ether (50 mL) and filtered through a pad of Celite. The filtrate was concentrated in vacuo and the residue was purified by flash chromatography to give 6-methoxy-1H-indazole-3-carbaldehyde (0.100 g, 56%).

The resulting product was coupled with 3,4,5-trimethoxybromobenzene and subsequently oxidized by $MnO_2$ in a manner similar to that described in Example 1 to afford compound 3 at a yield of 54%.

$^1H$ NMR (300 MHz, $CDCl_3$) δ 3.89 (s, 3H, —$OCH_3$), 3.93 (s, 6H, —$OCH_3$), 3.94 (s, 3H, —$OCH_3$), 6.90 (d, 1H, J=2.1 Hz), 7.01 (dd, 1H, J=9, 2.1 Hz), 7.665 (s, 2H), 8.27 (d, 1H, J=9 Hz), 10.44 (s, 1H).

Example 4

Synthesis of (6-methoxy-indolizin-1-yl)-(3,4,5-trimethoxy-phenyl)-methanone (compound 4)

Potassium tert-butoxide (5.4 g, 48 mmol) was added to 3-methyl-pyridin-3-ol (5 g, 45.87 mmol) in THF (200 mL) at 0° C. The mixture was stirred at room temperature for 30 min. MeI (3.2 mL, 48 mmol) was added dropwise at 0° C. and stirring was continued at room temperature for 8 h. Water was added and the mixture was evaporated to half its volume and extracted with EtOAc. The organic layer was washed with brine and water, dried over anhydrous $MgSO_4$, and filtered. The filtrate was concentrated in vacuo, and the residue was purified by flash chromatography to give 5-methoxy-2-methyl-pyridine (4.8 g, 85%).

n-BuLi in hexane (1.6 M, 7.6 mL, 11.9 mmol) was added dropwise to a solution of diisopropylamine (1.089 g, 10.9 mmol) in THF (25 mL) at −60 to −70° C. under $N_2$. The mixture was stirred for 10 min. A solution of 5-methoxy-2-methyl-pyridine (1.274 g, 10.35 mmol) in THF (5 mL) was added dropwise to the above mixture. Stirring was continued for another 10 min and 3,4,5-trimethoxybenzonitrile (1.88 g, 9.74 mmol) in THF (5 mL) was added at −70° C. The mixture was stirred at −78° C. for 1 h and then allowed to warm to room temperature. Stirring was continued for another 2 h and the reaction mixture was poured into an ice-cold aqueous $NH_4Cl$ solution. The organic layer was separated and the aqueous phase was extracted with ether. The combined organic layers were extracted with a dilute HCl solution. The aqueous layer was washed with ether, neutralized with 10% aqueous NaOH, and extracted with ether. The organic layer was washed with water and dried. The residue was purified by chromatography eluting with $CH_2Cl_2$ to give 2-(5-methoxy-pyridin-2-yl)-1-(3,4,5-trimethoxyphenyl)ethanone (2.31 g, 75.0%).

A mixture of the resulting pyridine derivative (0.200 g, 0.631 mmol), chloroacetaldehyde (0.099 g, 1.3 mmol), and NaHCO$_3$ (0.212 g, 2.6 mmol) in acetone (5 mL) was refluxed for 20 h. The precipitate was removed by filtration. The filtrate was concentrated to give a residue, which was purified on a silica gel column eluting with CH$_2$Cl$_2$ to afford compound 4 (0.184 g, 95%).

$^1$H NMR (300 MHz, CDCl$_3$) δ 3.86 (s, 3H, —OCH$_3$), 3.91 (s, 6H, —OCH$_3$), 3.93 (s, 3H, —OCH$_3$), 7.00 (dd, 1H, J=9.6, 1.5 Hz), 7.08 (d, 1H, J=3 Hz), 7.10 (s, 2H), 7.62 (d, 1H, J=1.5 Hz), 8.37 (d, J=1H, 9.6 Hz).

Example 5

Synthesis of (6-methoxy-2-methyl-indolizin-1-yl)-(3,4,5-trimethoxy-phenyl)-methanone (compound 5)

A mixture of 2-(5-methoxypyridin-2-yl)-1-(3,4,5-trimethoxyphenyl)ethanone (0.200 g, 0.631 mmol), 1-bromo-2-propanone (0.171 g, 1.3 mmol), and NaHCO$_3$ (0.212 g, 2.6 mmol) in acetone (5 mL) was refluxed for 20 h. The precipitate was removed by filtration. The filtrate was concentrated to give a residue, which was purified on a silica gel column eluting with CH$_2$Cl$_2$ to afford compound 5 (0.213 g, 95%).

$^1$H NMR (300 MHz, CDCl$_3$) δ 2.29 (s, 3H, —CH$_3$), 3.81 (s, 3H, —OCH$_3$), 3.85 (s, 6H, —OCH$_3$), 3.92 (s, 3H, —OCH$_3$), 6.74 (dd, 1H, J=9.6, 2.1 Hz), 6.97 (s, 2H), 7.08 (s, 1H), 7.40 (d, 1H, J=9.6 Hz), 7.50 (d, 1H, J=2.1 Hz).

Example 6

Synthesis of (2-ethyl-6-methoxy-indolizin-1-yl)-(3,4,5-trimethoxy-phenyl)-methanone (compound 6)

A mixture of A mixture of 2-(5-methoxypyridin-2-yl)-1-(3,4,5-trimethoxyphenyl)ethanone (0.200 g, 0.631 mmol), 1-bromo-2-butanone (0.190 g, 1.3 mmol), and NaHCO$_3$ (0.212 g, 2.6 mmol) in acetone (5 mL) was heated under reflux for 20 h. The precipitate was removed by filtration. The filtrate was concentrated to give a residue, which was purified on a silica gel column eluting with CH$_2$Cl$_2$ to afford compound 6 (0.213 g, 92%).

$^1$H NMR (300 MHz, CDCl$_3$) δ 1.23 (t, 3H, —CH$_2$CH$_3$, J=7.5 Hz), 2.79 (q, 2H, —CH$_2$CH$_3$, J=7.5 Hz), 3.81 (s, 3H, —OCH$_3$), 3.84 (s, 6H, —OCH$_3$), 3.92 (s, 3H, —OCH$_3$), 6.71 (dd, 1H, J=9.9, 2.1 Hz), 6.97 (s, 2H), 7.13 (s, 1H), 7.31 (d, 1H, J=9.9 Hz), 7.52 (d, 1H, J=2.1 Hz).

Example 7

Synthesis of (7-methoxy-2-methyl-indolizin-3-yl)-(3,4,5-trimethoxy-phenyl)-methanone (compound 7)

Methylzinc chloride in THF (2 M, 10.489 mL, 21 mmol) was added to a solution of 2-chloro-4-methoxypyridine (0.500 g, 3.48 mmol) and Pd(PPh$_3$)$_4$ (0.161 g, 0.14 mmol) in THF (10 mL). The mixture was refluxed for 40 h and then poured into an aqueous solution (10 mL) containing ethylenediaminetetraacetic acid (1.5 g). The resulting mixture was neutralized with K$_2$CO$_3$ and extracted with Et$_2$O. The organic layer was concentrated to give a residue, which was purified on a silica gel column eluting with MeOH:EtOAc (1:10) to give 4-methoxy-2-methylpyridine (0.213 g, 50.0%).

4-Methoxy-2-methylpyridine (0.123 g, 1 mmol) and bromoacetone (0.16 mL, 1 mmol) were heated at 95° C. under N$_2$ for 2 h. 1,8-Diazabicyclo-[5.4.0]-undec-7-ene (0.34 mL, 2.2 mmol) in benzene (10 mL) was added. The mixture was then refluxed under N$_2$ for 1 h, poured into ice water, and then extracted with EtOAc. The combined organic layers were washed with water and dried. After the solvent was removed in vacuo, the residue was purified on a silica gel column eluting with EtOAc:Hexane (1:9) and EtOAc to give 7-methoxy-2-methylindolizine (0.050 g, 31%).

A mixture of the indolizine 7-methoxy-2-methylindolizine (0.040 g, 0.25 mmol, 1 eq.), substituted benzoyl chloride (2.0 eq.), and Et$_3$N (5.0 eq.) was heated at 90° C. (bath temperature) for 2-8 h. The reaction mixture was cooled to room temperature, and EtOAc was added. The organic layer was separated and washed with dilute HCl and water and dried. After the solvent was removed, the residue was purified on a silica gel column eluting with EtOAc:hexane (1:9) to give compound 7 (0.065 g, 74%).

$^1$H NMR (300 MHz, CDCl$_3$) δ 1.97 (s, 3H, —CH$_3$), 3.91 (s, 3H, —OCH$_3$), 3.88 (s, 9H, —OCH$_3$), 6.15 (s, 1H), 6.54 (dd, 1H, J=7.8, 2.7 Hz), 6.69 (d, 1H, J=2.7 Hz), 6.85 (s, 2H), 9.62 (s, 1H)

Example 8

Synthesis of (6-methyl-1H-pyrrolo[2,3-b]pyridin-3-yl)-(3,4,5-trimethoxy-phenyl)-methanone (compound 8)

6-Chloro-1-(phenylsulfonyl)-1H-pyrrolo[2,3-b]pyridine was prepared by the method described in Samuel C. et al., *Heterocycles*, 1990, 30 (1), 627-633.

A solution of methylzinc chloride in THF (2 M) (9 mL, 12 mmol) was added to 6-chloro-1-(phenylsulfonyl)-1H-pyrrolo[2,3-b]pyridine (0.600 g, 2.05 mmol) and Pd(PPh$_3$)$_4$ (0.095 g, 0.08 mmol) in THF (30 mL). The mixture was refluxed for 40 h, cooled to 0° C., quenched with water and extracted with Et$_2$O. The organic layer was concentrated and the residue was purified over a silica gel column eluting with EtOAc/hexane (1:5) to give N-protected 6-methyl-7-azaindole (0.495 g, 88%).

A solution of 50% NaOH (0.573 g) was added to N-protected 6-methyl-7-azaindole (0.390 g, 1.43 mmol) in Ethanol (10 mL). After refluxed for 8 h, the mixture was concentrated and was extracted with CHCl$_3$. The organic layer was washed with water and dried. The solvent was evaporated in vacuo and the residue was purified on a silica gel column eluting with EtOAc/hexane (1:3) to give 6-methyl-1H-pyrrolo[2,3-b]pyridine (0.148 g, 78%).

Ethylmagnesium bromide (3.0 M solution in diethyl ether, 0.43 mL) was added to a mixture of 6-methyl-1H-pyrrolo[2,3-b]pyridine (0.127 g, 0.969 mmol) and anhydrous zinc chloride (0.263 g, 1.94 mmol) in dry CH$_2$Cl$_2$ (20 mL) over 10 min at room temperature. The suspension was stirred for 1 h and then a solution of 3,4,5-trimethoxybenzoyl chloride (0.335 g, 1.45 mmol) in dry CH$_2$Cl$_2$ (10 mL) was added dropwise over 5 min. After 1 h, aluminum chloride (0.129 g, 0.969 mmol) was added. The resulting thick mixture was vigorously stirred for 5 h. The reaction was quenched with water (10 mL) and extracted with CH$_2$Cl$_2$ (20 mL). The organic layer was dried over anhydrous MgSO$_4$ and concentrated to give a brown oil, which was further purified on a silica gel column (MeOH:CH$_2$Cl$_2$=1:25) to give compound 8 (0.150 g, 48%) as a white solid.

$^1$H NMR (300 MHz, CDCl$_3$) δ 2.76 (s, 3H, —CH$_3$), 3.92 (s, 6H, —OCH$_3$), 3.96 (s, 3H, —OCH$_3$), 7.17 (s, 2H), 7.21 (d, 1H, J=8.1 Hz), 7.90 (s, 1H), 8.59 (d, 1H, J=8.1 Hz), 13.29 (s, 1H)

Example 9

Synthesis of (6-methoxy-1H-pyrrolo[2,3-b]pyridin-3-yl)-(3,4,5-trimethoxy-phenyl)-methanone (compound 9)

7-Azaindole N-oxide was prepared by the method described in Minakata et al., *Synthesis*, 1992, 7, 661-663.

A mixture of 7-azaindole N-oxide (5.55 g, 8.6 mmol) in $Ac_2O$ (30 mL) was refluxed for 12 h. The reaction mixture was concentrated to half its volume, extracted with $CH_2Cl_2$, washed with water, dried over anhydrous $MgSO_4$, and evaporated to give a residue, which was purified on a column of silica gel eluting with EtOAc/hexane (1:6) to give 1-acetyl-1H-pyrrolo[2,3-b]pyridin-6-yl acetate (4.55 g, 70%).

A mixture of 1-acetyl-1H-pyrrolo[2,3-b]pyridin-6-yl acetate (0.635 g, 2.9 mmol) and $K_2CO_3$ (1.6 g, 12 mmol) in $MeOH/H_2O$ (20 mL/20 mL) was stirred at room temperature for 12 h. The reaction mixture was concentrated to half its volume and extracted with $CHCl_3$. The organic layer was dried over anhydrous $MgSO_4$ and evaporated to give a residue, which was further purified on a silica gel column to give 1H-pyrrolo[2,3-b]pyridin-6-ol (0.233 g, 60%).

A mixture of 1H-pyrrolo[2,3-b]pyridin-6-ol (0.200 g, 1.49 mmol) and $K_2CO_3$ (1 g, 7.45 mmol) in acetone (30 mL) was stirred under $N_2$ at room temperature for 1 h. MeI (0.166 g, 1.192 mmol) was added. The reaction mixture was stirred under $N_2$ at 50° C. for 12 h and then filtered. The filtrate was concentrated to half its volume, diluted with water, and extracted with $CH_2Cl_2$. The organic layer was dried over anhydrous $MgSO_4$, and evaporated to give a residue, which was purified on a column of silica gel eluting with EtOAc/hexane (1:4) to give 6-methoxy-1H-pyrrolo[2,3-b]pyridine (159 mg, 89%).

Ethylmagnesium bromide (3.0 M solution in diethyl ether, 0.33 mL) was added to a mixture of 6-methoxy-1H-pyrrolo[2,3-b]pyridine (0.108 g, 0.73 mmol) and anhydrous zinc chloride (0.201 g, 1.46 mmol) in dry $CH_2Cl_2$ (20 mL) over 10 min at room temperature. The suspension was stirred for 1 h and 3,4,5-trimethoxybenzoyl chloride (0.252 g, 1.09 mmol) in dry $CH_2Cl_2$ (10 mL) was then added dropwise over 5 min. After the reaction mixture was stirred for 1 h, aluminum chloride (0.097 g, 0.73 mmol) was added. The resulting thick mixture was vigorously stirred for 5 h. The reaction was quenched with water (10 mL) and extracted with $CH_2Cl_2$ (20 mL). The combined organic layers were dried over anhydrous $MgSO_4$ and evaporated to give a brown oil, which was purified on a silica gel column eluting with EtOAc/hexane (1:1) to compound 9 (0.189 g, 76%).

$^1H$ NMR (300 MHz, $CDCl_3$) δ 3.91 (s, 6H, —$OCH_3$), 3.94 (s, 3H, —$OCH_3$), 3.99 (s, 3H, —$OCH_3$), 6.78(d, 1H, J=8.7 Hz), 7.12 (s, 2H), 7.64(d, 1H, J=3 Hz), 8.49(d, 1H, J=8.7 Hz), 9.09 (s, 1H)

Example 10

Synthesis of (6-ethoxy-1H-pyrrolo[2,3-b]pyridin-3-yl)-(3,4,5-trimethoxy-phenyl)-methanone (compound 10)

Compound 10 was prepared by the same method described in Example 9 except EtI, instead of MeI, was used.

$^1H$ NMR (300 MHz, $CDCl_3$): δ 1.45(t, 1H, —$OCH_2CH_3$, J=6.9 Hz), 3.91 (s, 3H, —$OCH_3$), 3.93 (s, 3H, —$OCH_3$), 3.94 (s, 3H, —$OCH_3$), 4.39(q, 2H, —$OCH_2CH_3$, J=6.9 Hz), 6.76 (d, 1H, J=9 Hz), 7.12 (s, 2H), 7.62(d, 1H, J=3 Hz), 8.48(d, 1H, J=9 Hz), 8.93 (s, 1H)

Example 11

Synthesis of (6-methoxy-3a,7a-dihydro-benzofuran-3-yl)-(3,4,5-trimethoxy-phenyl)-methanone (compound 11)

A mixture of (6-methoxy-benzofuran-3-yl)-acetic acid (2 g, 9.7 mmol) and $H_2SO_4$ (0.3 mL) in methanol (40 mL) was refluxed for 8 h and then concentrated. An aqueous $NaHCO_3$ solution was added, followed by extraction with $CH_2Cl_2$. The combined organic layers were dried over anhydrous $MgSO_4$ and evaporated to give a brown oil, which was purified on a silica gel column eluting with EtOAc/hexane (1:10) to give methyl 2-(6-methoxybenzofuran-3-yl)acetate (2.1 g, 98%)

A mixture of methyl 2-(6-methoxybenzofuran-3-yl)acetate (0.500 g, 2.27 mmol) and $SeO_2$ (0.303 g, 2.73 mmol) in 1,4-dioxane (10 mL) was refluxed for 2 days and then filtered. The filtrate was concentrated in vacuo and the residue was purified on a silica gel column to give methyl 2-(6-methoxy-benzofuran-3-yl)-2-oxoacetate (0.452 g, 85%)

LAH (0.093 g, 2.39 mmol) was added to a mixture of methyl 2-(6-methoxybenzofuran-3-yl)-2-oxoacetate (0.280 g, 1.196 mmol) in THF (10 mL) at 0° C. under $N_2$, and the mixture was stirred overnight at room temperature under $N_2$. An aqueous $NH_4Cl$ solution (5 mL) was added, and the reaction mixture was concentrated to half its volume and extracted with EtOAc. The organic layer was washed with brine and water, dried over anhydrous $MgSO_4$, and evaporated to give 1-(6-methoxy-benzofuran-3-yl)-ethane-1,2-diol.

$NaIO_4$ (0.204 g, 1.12 mmol) was added to 1-(6-methoxy-benzofuran-3-yl)-ethane-1,2-diol (0.180 g, 1.196 mmol) in THF (50 mL) and water (1 mL) with stirring. The mixture was stirred overnight at room temperature under $N_2$. Water (10 mL) was added, and the mixture was concentrated to half its volume and extracted with EtOAc. The organic layer was washed with brine and water, dried over anhyd. $MgSO_4$, and evaporated to give a residue, which was purified on a silica gel column eluting with EtOAc/hexane (1:10) to give 6-methoxybenzofuran-3-carbaldehyde (0.110 g, 73%).

To a dry flask equipped with a condenser, an addition funnel, and a magnetic stirrer were added magnesium turnings (2.5 mmol), THF (0.5 mL), and a small piece of iodine. To this was added via the addition funnel approximately ⅓ of 3,4,5-trimethoxybromobenzene (2.5 mmol) in 1.3 mL of THF. When the solution became colorless (heating may be needed), the remaining 3,4,5-trimethoxybromobenzene solution was added dropwise to the solution under mild refluxing. Stirring was then continued for 1 h at room temperature. The resulting solution was then slowly added to 6-methoxybenzofuran-3-carbaldehyde (0.100 g, 0.176 mmol) in anhydrous THF (5 mL) at 0° C. After the addition, the solution was allowed to stir at room temperature for another 20 min. Then, a saturated $NH_4Cl$ solution (5 mL) was slowly added at 0° C., and the mixture was stirred for 10 min. The aqueous layer was separated and extracted with $Et_2O$ (3×10 mL). The combined organic layers were washed with brine, dried over $MgSO_4$, and filtered. The filtrate was concentrated in vacuo and the residue was purified by column chromatography to provide benzhydrol (0.097 g, 50%).

$MnO_2$ (0.193 g, 1.88 mmol) was added to a solution of benzhydrol (0.050 g, 0.145 mmol) in 5 mL anhydrous $CH_2Cl_2$ at 0° C. with stirring. After the addition, the mixture was stirred at room temperature for 8 h. The mixture was diluted with anhydrous ether (50 mL) and filtered through a pad of Celite. The filtrate was concentrated in vacuo and the residue was purified by flash chromatography to give compound 11 (0.043 g, 87%)

$^1$H NMR (300 MHz, CDCl$_3$) δ 3.89 (s, 3H, —OCH$_3$), 3.92 (s, 6H, —OCH$_3$), 3.95 (s, 3H, —OCH$_3$), 7.03(dd, 1H, J=8.4, 2.1 Hz), 7.08(d, 1H, J=2.1 Hz), 7.16 (s, 2H), 8.03(s, 1H), 8.05 (d, 1H, J=9.3 Hz).

Example 12

Synthesis of (6-methoxy-2-methyl-3a,7a-dihydro-benzofuran-3-yl)-(3,4,5-trimethoxy-phenyl)-methanone (compound 12)

A mixture of 6-methoxybenzofuran-3-carbaldehyde (0.600 g, 3.41 mmol), HOCH$_2$CH$_2$OH (3.17 g, 51 mmol) and p-toluenesulfonic acids (0.001 g) in benzene (20 mL) was refluxed for 8 h using a Dean-Stark water trap. The mixture was concentrated under reduced pressure and then diluted with EtOAc. The organic solution was washed with water, dried over anhydrous MgSO$_4$, and concentrated to give 3-(1, 3-dioxolan-2-yl)-6-methoxybenzofuran (0.711 g, 95%)

3-(1,3-Dioxolan-2-yl)-6-methoxybenzofuran (0.144 g, 0.65 mmol) was dissolved in THF (5 mL) at −30 to −20° C. To this solution was added dropwise tert-butyllithium (15% in pentane, 0.56 mL, 1.31 mmol). The reaction mixture was continuously stirred at −30° C. for 30 min and then allowed to warm to 0° C. and stir for another 20 min. The reaction mixture was cooled to −30° C. again and iodomethane (0.138 g, 0.98 mmol) was added dropwise. After stirring at −30° C. for another 1 h, it was allowed to warm to room temperature overnight. After the solvent was removed under reduced pressure, the residue was dissolved in EtOAc and washed with saturated NaHCO$_3$. The aqueous layer was extracted with EtOAc (3×20 mL). The combined organic layers were dried over anhydrous MgSO$_4$ and concentrated under reduced pressure to provide 3-[1,3]dioxolan-2-yl-6-methoxy-2-methyl-benzofuran.

2N HCl (5 mL) was added to 3-[1,3]dioxolan-2-yl-6-methoxy-2-methyl-benzofuran in THF (5 mL) at 0° C. After stirring for 1 h at room temperature, the solvent was removed under reduced pressure. The residue was dissolved in EtOAc and washed with saturated NaHCO$_3$. The aqueous layer was extracted with EtOAc (3×20 mL). The organic layers were combined and dried over anhydrous MgSO$_4$. After the solvent was removed, the residue was purified on a silica gel column eluting with EtOAc/hexane (1:9) to give 6-methoxy-2-methylbenzofuran-3-carbaldehyde (0.090 g, 81%).

6-Methoxy-2-methylbenzofuran-3-carbaldehyde was coupled with 3,4,5-trimethoxybromobenzene and subsequently oxidized by MnO$_2$ in a manner similar to that described in Example 11 to afford compound 12.

$^1$H NMR (300 MHz, CDCl$_3$) δ 2.55 (s, 3H, —CH$_3$), 3.85 (s, 6H, —OCH$_3$), 3.86 (s, 3H, —OCH$_3$), 3.95 (s, 3H, —OCH$_3$), 6.85 (dd, 1H, J=9, 2.4 Hz), 7.01(d, 1H, J=2.4 Hz), 7.12 (s, 2H), 7.34 (d, 1H, J=9 Hz).

Example 13

Synthesis of (6-methoxy-3a,7a-dihydro-benzo[b]thiophen-3-yl)-(3,4,5-trimethoxy-phenyl)-methanone (compound 13)

6-Methoxy-3-methylbenzo[b]thiophene was prepared using the method described in Campaigne et al., *J Heterocycl Chem*, 1970, 7, 695.

A mixture of 6-methoxy-3-methylbenzo[b]thiophene (2.753 g, 15.5 mmol) and SeO$_2$ (2.06 g, 18.55 mmol) in 1,4-dioxane (30 mL) was refluxed for 2 days and then filtered. The filtrate was concentrated in vacuo, and the residue was purified on a silica gel column eluting with EtOAc/hexane (1:10) to give 6-methoxybenzo[b]thiophene-3-carbaldehyde (2.3 g, 80%).

The resulting product was then coupled with 3,4,5-trimethoxybromobenzene and then oxidized by MnO$_2$ in a manner similar to that described in Example 11 to afford compound 13 at a yield of 54%.

$^1$H NMR (300 MHz, CDCl$_3$) δ 3.89 (s, 6H, —OCH$_3$), 3.91 (s, 3H, —OCH$_3$), 3.95 (s, 3H, —OCH$_3$), 7.13 (dd, 1H, J=9, 2.4 Hz), 7.14 (s, 2H), 7.36(d, 1H, J=2.4 Hz), 7.85 (s, 1H), 8.37 (d, 1H, J=9 Hz).

Example 14

Synthesis of (6-methoxy-2-methyl-3a,7a-dihydro-benzo[b]thiophen-3-yl)-(3,4,5-trimethoxy-phenyl)-methanone (compound 14)

6-Methoxybenzo[b]thiophene-3-carbaldehyde was converted to 3-(1,3-dioxolan-2-yl)-6-methoxybenzo[b]thiophene according to the method described in Example 12.

The resulting product was then coupled with 3,4,5-trimethoxybromobenzene and then oxidized by MnO$_2$ in a manner similar to that described in Example 11 to afford compound 14 at a yield of 79%.

$^1$H NMR (300 MHz, CDCl$_3$) δ 2.49 (s, 3H, —CH$_3$), 3.82 (s, 6H, —OCH$_3$), 3.87 (s, 3H, —OCH$_3$), 3.95 (s, 3H, —OCH$_3$), 6.92 (dd, 1H, J=9, 2.4 Hz), 7.12 (s, 2H), 7.26(d, 1H, J=2.4 Hz), 7.44 (d, 1H, J=9 Hz).

Example 15

Synthesis of (6-methoxy-pyrazolo[1,5-b]pyridazin-3-yl)-(3,4,5-trimethoxy-phenyl)-methanone (compound 15)

A solution of 3,4,5-trimethoxybenzaldehyde (1.0 g, 5.0 mmol) in THF (50 mL) was stirred at 0° C. Sodium acetylide (18% w.t. slurry in xylene, 1.63 g, 6.1 mmol) was added via syringe. The reaction mixture was stirred overnight at room temperature and quenched by water. It was then extracted with EtOAc (30 mL×3). The combined organic layers were washed with brine, dried over anhydrous MgSO$_4$, filtered, and concentrated to give a crude product, which was purified by flash column chromatography eluting with EtOAc/n-hexane (1:2) to afford 1-(3,4,5-trimethoxyphenyl)prop-2-yn-1-ol as a white solid (815 mg, 72%).

To a stirred solution of 1-(3,4,5-trimethoxyphenyl)prop-2-yn-1-ol (100 mg, 0.44 mmol) in acetone (10 mL), aqueous Jones reagent was added dropwise at 0° C. until the red color persisted. The reaction mixture was quenched by 2-propanol, and the precipitate was were removed by filtered through Celite. The filtrate was diluted with EtOAc, washed several times with a saturated aqueous NaHCO$_3$ solution, water and brine, dried over MgSO$_4$, and concentrated to give crude product, which was purified by flash chromatography eluting with EtOAc/n-hexane (1:4) to afford 1-(3,4,5-trimethoxyphenyl)prop-2-yn-1-one as a colorless oil (74 mg, 75%).

A mixture of 3-chloro-6-methoxypyridazine (1.0 g, 6.9 mmol) in methanol (50 mL) with 33% palladium on carbon (100 mg) was hydrogenated under 45 psi overnight. The catalyst was removed by filtration through a pad of Celite. The filtrate was concentrated and dissolved in EtOAc. The solution was washed several times with a saturated NaHCO$_3$ solution and brine, dried over MgSO$_4$, concentrated to give a crude product, which was purified on a silica gel column eluting with EtOAc/n-hexane (1:2) to give 3-methoxypyridazine as a pale yellow solid (662 mg, 87%).

$^1$H NMR (300 MHz, CDCl$_3$): δ 4.14 (s, 3H), 6.98 (dd, J=1.2, 9.0 Hz, 1H), 7.36 (dd, J=4.5, 8.7 Hz, 1H), 8.84 (dd, J=1.2, 4.5 Hz, 1H).

Potassium bicarbonate (2.5 M) was added to a solution of hydroxylamine-O-sulfonic acid (64.7 mg, 0.57 mmol) until the pH value turned to 5. Then, 3-methoxypyridazine (42 mg, 0.38 mmol) was added at 70° C. over 10 min. The mixture was stirred at 70° C. for 2 h and then cooled to room temperature. The pH value of the mixture was adjusted to 8 by addition of 2.5M potassium bicarbonate. 1-(3,4,5-Trimethoxyphenyl) prop-2-yn-1-one (42 mg, 0.19 mmol) in CH$_2$Cl$_2$ (10 mL) and potassium hydroxide (40 mg, 0.71 mmol) were added. The mixture was stirred at room temperature overnight, and then was extracted with CH$_2$Cl$_2$, and the combined organic layers were washed with brine, dried over MgSO$_4$, and concentrated to give a crude product, which was purified on a silica gel column eluting with CH$_2$Cl$_2$/MeOH (20:1) to afford compound 15 as a white solid (31 mg, 48%).

$^1$H NMR (300 MHz, CDCl$_3$): δ 3.93 (s, 6H), 3.95 (s, 3H), 4.11 (s, 3H), 7.00 (d, J=9.3 Hz, 1H), 7.15 (s, 2H), 8.23 (s, 1H), 8.56 (d, J=9.6 Hz, 1H).

Example 16

Synthesis of (2-methoxy-7H-pyrrolo[2,3-d]pyrimidin-5-yl)-(3,4,5-trimethoxy-phenyl)-methanone (compound 16)

10% Pd/C (1.000 g, 11.6 mmol) was added to a solution of 4-chloro-2-methoxy-7H-pyrrolo[2,3-d]pyrimidine (0.200 g, 1.09 mmol) in 20 mL anhydrous MeOH under H$_2$ at room temperature. The mixture was stirred for 8 h and then filtered through a pad of Celite. The filtrate was concentrated in vacuo to give 2-methoxy-6,7-dihydro-5H-pyrrolo[2,3-d]pyrimidine as a major product.

MnO$_2$ (1.720 g, 20 mmol) was added to 2-methoxy-6,7-dihydro-5H-pyrrolo[2,3-d]pyrimidine in 20 mL of anhydrous CH$_2$Cl$_2$ at room temperature. The mixture was stirred for 8 h, diluted with anhydrous ether (50 mL), and filtered through a pad of Celite. The filtrate was concentrated in vacuo, and the residue was purified on a silica gel column eluting with MeOH/CH$_2$Cl$_2$ (1:9) to give 2-methoxy-7H-pyrrolo[2,3-d]pyrimidine (0.149 g, 90%).

To a mixture of 2-methoxy-7H-pyrrolo[2,3-d]pyrimidine (0.220 g, 1.476 mmol) and anhydrous zinc chloride (0.407 g, 2.953 mmol) in dry CH$_2$Cl$_2$ (20 mL), ethylmagnesium bromide (0.65 mL, 3.0 M solution in diethyl ether) was added over 10 min at room temperature. The suspension was stirred for 1 h, and then 3,4,5-trimethoxybenzoyl chloride (0.510 g, 2.2 mmol) in dry CH$_2$Cl$_2$ (10 mL) was added dropwise over 5 min. The reaction mixture was stirred for another 1 h and then aluminum chloride (0.196 mg, 1.476 mmol) was added. The resulting thick mixture was vigorously stirred for 5 h. The reaction was quenched with water (10 mL) and extracted with CH$_2$Cl$_2$ (20 mL). The combined organic layers were dried over anhydrous MgSO$_4$ and evaporated to give a brown oil, which was purified on a silica gel column (EtOAc:Hexane=1:1 to MeOH:CH$_2$Cl$_2$=1:20) to give compound 16 (0.081 g, 20%).

$^1$H NMR (300 MHz, CDCl$_3$) δ 3.93 (s, 6H, —OCH$_3$), 3.95 (s, 3H, —OCH$_3$), 4.09 (s, 3H, —OCH$_3$), 7.13 (s, 2H), 7.71(d, 1H, J=2.4 Hz), 9.38 (s, 1H), 9.79 (s, 1H).

Example 17

Cell Growth Inhibition Assay

KB cells (a cell line derived from a human carcinoma of the nasopharynx) and MKN-45 cells (a gastric cancer cell line) were maintained in plastic dishes in RPMI 1640 medium supplemented with 5% fetal bovine serum. The KB cells were seeded in 96-well plates at a final cell density of 7,000 cell/mL. The MKN-45 cells were seeded in 96-well plates at a final cell density of 20,000 cell/mL. The cells were treated with a test compound (at least five different concentrations for the test compound), and incubated in a CO$_2$ incubator at 37° C. for 72 h. The number of viable cells was estimated using the MTS assay (or the methylene blue assay) and absorbance was measured at 490 nm. Cytotoxicity of the test compounds was expressed in terms of IC$_{50}$ values. The values represent averages of three independent experiments, each with duplicate samples.

Compounds 1-14 were tested in the above assay. All of them effectively inhibited growth of KB cells and MKN-45 cells. Unexpectedly, most of them exhibited IC$_{50}$ values lower than 1 mM, some even lower than 100 nM.

Example 18

Tubulin Polymerization Assay

Turbidimetric assays of microtubule are performed according to the procedure described by Lopes et al. (1997, Cancer Chemother. Pharmacol. 41: 37-47) with some modifications. MAP-rich tubulin (2 mg/ml) is preincubated in a polymerization buffer (0.1 M PIPES, pH 6.9, 1 mM MgCl$_2$) with a test compound at 4° C. for 2 min before the addition of 1 mM GTP. The samples are then rapidly warmed to 37° C. in a 96-well plate thermostatically controlled spectrophotometer and measuring the change at 350 nm with time.

Example 19

Cell Growth Inhibition Assay on Multiple-Drug Resistant Human Cancer Cell Lines

Several fused bicyclic heteroaryl compounds of this invention are tested against several panels of drug-resistant cell lines. It is well known that several anti-mitotic agents, including vinca alkaloid (e.g., vincristine and vinblastine) and taxol, have been used to treat various human cancers. Vinca alkaloid resistance has been attributed to a number of mechanisms associated with the multi-drug resistance (MDR) phenotype, including overexpression of p-glycoprotein and multi-drug resistant-associated protein (MRP). The mechanisms responsible for taxol resistance include overexpression of p-glycoprotein and mutation of tubulin. For comparison, five anti-mitotic agents, i.e., vincristine, VP-16, cisplatin, camptothecin, and taxol, are also tested against several panels of drug-resistant cell lines e.g., KB-Vin10 (a vincristine-resistant cell line), KB100 (a camptotnecin-resistant cell line), and CPT30 (a camptothecin-resistant cell line).

Example 20

CAM Assay for Antiangiogenic Potency

Each test compound is dissolved in a 2.5% aqueous agarose solution (final concentration: 1-20 mg/mL). 10 µL of the solution are applied dropwise on circular Teflon pallets of 3 mm in diameter and then cooled to room temperature at once. After incubation at 37° C. and relative humidity of 80% for 65-70 h, fertilized hen eggs are positioned in a horizontal position and rotated several times. Before opening the snub side, 10 mL of albumin are aspirated from a hole on the pointed side. At two-third of the height (from the pointed side), the eggs are traced with a scalpel and the shells are removed with forceps. After the aperture (cavity) has been covered with keep-fresh film, the eggs are incubated at 37° C. at a relative humidity of 80% for 75 h. When the chorioallantoic membrane approximates a diameter of 2 cm, one pellet (1 pellet/egg) is placed on it. The eggs are incubated for 1 day and subsequently evaluated under the stereomicroscope.

Other Embodiments

All of the features disclosed in this specification may be combined in any combination. Each feature disclosed in this specification may be replaced by an alternative feature serving the same, equivalent, or similar purpose. Thus, unless expressly stated otherwise, each feature disclosed is only an example of a generic series of equivalent or similar features.

From the above description, one skilled in the art can easily ascertain the essential characteristics of the present invention, and without departing from the spirit and scope thereof, can make various changes and modifications of the invention to adapt it to various usages and conditions. For example, compounds structurally analogous to the fused bicyclic heteroaryl compounds of this invention also can be made, screened for their inhibitory activities against cancer cell growth, and used to practice this invention. Thus, other embodiments are also within the claims.

What is claimed is:

1. A compound of the following formula:

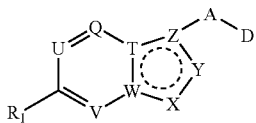

in which
each ═ is a single bond or a double bond;
A is C(═O), CRR', O, NR, or S;
D is aryl or hetereoaryl;
$R_1$ is selected from alkyl, alkoxy, and amino;
each of Q, U, and V, independently, is CR or N;
X is N or NR' and Y is CR; or X is CR, and Y is N;
Z is C; and
each of T and W is C or N, at least one of T and W being C;
provided that
when T is C and W is N, the bond between T and W is a single bond, the bond between T and Z is a double bond, the bond between Y and Z is a single bond, the bond between X and Y is a double bond, the bond between W and X is a single bond, and X is N or CR;
when T is N and W is C, the bond between T and W is a single bond, the bond between T and Z is a single bond, the bond between Y and Z is a double bond, the bond between X and Y is a single bond, the bond between W and X is a double bond, and X is N or CR; and
when T is C and W is C, the bond between T and W is a double bond, the bond between T and Z is a single bond, the bond between Y and Z is a double bond, the bond between X and Y is a single bond, the bond between W and X is a single bond and X is NR', Y is CR, and at least one of Q, U and V is N;
wherein each of R and R', independently, is H, alkyl, alkenyl, alkynyl, aryl, heteroaryl, cyclyl, heterocyclyl, $SO_3R_a$, $SO_2R_a$, $SO_2NR_aR_b$, $COR_a$, $COOR_a$, or $CONR_aR_b$; each $R_a$ and $R_b$, independently, is H, alkyl, alkenyl, alkynyl, aryl, heteroaryl, cyclyl, or heterocyclyl.

2. The compound of claim 1, wherein each of T and X is N, W is C, each of Q, U, and V is CH, and Y is CR.

3. The compound of claim 1, wherein each of T and W is C, each of Q and U is CH, V is N, X is NH, and Y is CR.

4. The compound of claim 1, wherein T is C, W is N, each of Q, U, and V, is CH, X is N, and Y is CR.

5. The compound of claim 1, wherein each of T and W is C, Q is CH, each of U and V is N, X is NH, and Y is CR.

6. The compound of claim 1, wherein T is C, each of W, V, and X is N, each of Q and U is CH, and Y is CR.

7. The compound of claim 1, wherein D is substituted phenyl.

8. The compound of claim 1, wherein D is 3,4,5-trimethoxyphenyl.

9. A compound of the following formula:

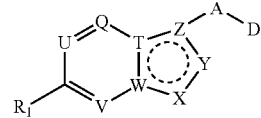

in which
each ═ is a single bond or a double bond;
A is C(═O), CRR', O, NR, S, SO, or $SO_2$;
D is aryl or hetereoaryl tri-substituted by alkoxy;
$R_1$ is selected from H, alkyl, aryl, alkoxy, hydroxy, halo, amino, and alkylamino;
each of Q, U, and V, independently, is CR or N;
X is N or NR' and Y is CR; or X is CR, and Y is N;
Z is C; and
each of T and W is C or N, at least one of T and W being C;
provided that
when T is C and W is N, the bond between T and W is a single bond, the bond between T and Z is a double bond, the bond between Y and Z is a single bond, the bond between X and Y is a double bond, the bond between W and X is a single bond, and X is N or CR;
when T is N and W is C, the bond between T and W is a single bond, the bond between T and Z is a single bond, the bond between Y and Z is a double bond, the bond between X and Y is a single bond, the bond between W and X is a double bond, and X is N or CR; and
when T is C and W is C, the bond between T and W is a double bond, the bond between T and Z is a single bond, the bond between Y and Z is a double bond, the bond between X and Y is a single bond, the bond between W and X is a single bond and X is NR', Y is CR, and at least one of Q, U and V is N;
wherein each of R and R', independently, is H, alkyl, alkenyl, alkynyl, aryl, heteroaryl, cyclyl, heterocyclyl, $SO_3R_a$, $SO_2R_a$, $SO_2NR_aR_b$, $COR_a$, $COOR_a$, or $CONR_aR_b$; each $R_a$ and $R_b$, independently, is H, alkyl, alkenyl, alkynyl, aryl, heteroaryl, cyclyl, or heterocyclyl.

10. The compound of claim 9, wherein each of T and X is N, W is C, each of Q, U, and V is CH, and Y is CR.

11. The compound of claim 9, wherein each of T and W is C, each of Q and U is CH, V is N, X is NH, and Y is CR.

12. The compound of claim 9, wherein T is C, W is N, each of Q, U, and V, is CH, X is N, and Y is CR.

13. The compound of claim 9, wherein each of T and W is C, Q is CH, each of U and V is N, X is NH, and Y is CR.

14. The compound of claim 9, wherein T is C, each of W, V, and X is N, each of Q and U is CH, and Y is CR.

15. The compound of claim 9, wherein D is 3,4,5-trimethoxyphenyl.

16. A pharmaceutical composition comprising a pharmaceutically acceptable carrier and a compound of claim 9.

17. A pharmaceutical composition comprising a pharmaceutically acceptable carrier and a compound of claim 1.

18. The composition of claim 17, wherein each of T and X is N, W is C, each of Q, U, and V is CH, and Y is CR.

19. The composition of claim 17, wherein each of T and W is C, each of Q and U is CH, V is N, X is NH, and Y is CR.

20. The composition of claim 17, wherein T is C, W is N, each of Q, U, and V, is CH, X is N, and Y is CR.

21. The composition of claim 17, wherein each of T and W is C, Q is CH, each of U and V is N, X is NH, and Y is CR.

22. The composition of claim 17, wherein T is C, each of W, V, and X is N, each of Q and U is CH, and Y is CR.

23. The composition of claim 17, wherein D is substituted phenyl.

24. The composition of claim 16, wherein D is 3,4,5-trimethoxyphenyl.

25. The composition of claim 16, wherein each of T and X is N, W is C, each of Q, U, and V is CH, and Y is CR.

26. The composition of claim 16, wherein each of T and W is C, each of Q and U is CH, V is N, X is NH, and Y is CR.

27. The composition of claim 16, wherein T is C, W is N, each of Q, U, and V, is CH, X is N, and Y is CR.

28. The composition of claim 16, wherein each of T and W is C, Q is CH, each of U and V is N, X is NH, and Y is CR.

29. The composition of claim 16, wherein T is C, each of W, V, and X is N, each of Q and U is CH, and Y is CR.

* * * * *